United States Patent
Schabbach

(10) Patent No.: US 8,974,747 B2
(45) Date of Patent: Mar. 10, 2015

(54) BODILY FLUID ANALYSIS DEVICE

(75) Inventor: Michael Schabbach, Frankfurt am Main (DE)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 0 days.

(21) Appl. No.: 14/007,178

(22) PCT Filed: Mar. 23, 2012

(86) PCT No.: PCT/EP2012/055256
§ 371 (c)(1),
(2), (4) Date: Sep. 24, 2013

(87) PCT Pub. No.: WO2012/130773
PCT Pub. Date: Oct. 4, 2012

(65) Prior Publication Data
US 2014/0018652 A1    Jan. 16, 2014

(30) Foreign Application Priority Data
Mar. 25, 2011 (EP) .................... 11159864

(51) Int. Cl.
| | | |
|---|---|---|
| G01N 33/00 | (2006.01) | |
| A61B 5/1477 | (2006.01) | |
| A61B 5/145 | (2006.01) | |
| A61B 5/1486 | (2006.01) | |
| A61B 5/1495 | (2006.01) | |
| A61B 5/15 | (2006.01) | |
| A61B 5/00 | (2006.01) | |

(52) U.S. Cl.
CPC ........... *A61B 5/1477* (2013.01); *A61B 5/14532* (2013.01); *A61B 5/1486* (2013.01); *A61B 5/14546* (2013.01); *A61B 5/1495* (2013.01); *A61B 5/150358* (2013.01); *A61B 5/72* (2013.01); *A61B 5/742* (2013.01); *A61B 2560/0209* (2013.01); *A61B 2560/0219* (2013.01); *A61B 2562/0209* (2013.01); *A61B 2562/0295* (2013.01); *A61B 2562/046* (2013.01)
USPC .................... 422/404; 422/82.01; 422/82.02; 422/68.1

(58) Field of Classification Search
USPC ............................ 422/404, 82.01, 82.02, 68.1
See application file for complete search history.

(56) References Cited

U.S. PATENT DOCUMENTS

| | | |
|---|---|---|
| 5,580,794 A | 12/1996 | Allen |
| 7,378,007 B2 | 5/2008 | Moerman et al. |
| 7,641,857 B2 | 1/2010 | Clemens et al. |
| 2007/0219574 A1 | 9/2007 | Freeman et al. |
| 2007/0227911 A1 | 10/2007 | Wang et al. |

FOREIGN PATENT DOCUMENTS

| WO | 2005084534 A1 | 9/2005 |
|---|---|---|

*Primary Examiner* — Sam P Siefke
(74) *Attorney, Agent, or Firm* — McDonnell Boehnen Hulbert & Berghoff LLP

(57) ABSTRACT

An apparatus comprising a substrate, the substrate having supported thereon:
  plural collectors each for collecting a bodily fluid from the surface of a body part placed adjacent thereto;
  an analyser for analysing each collected bodily fluid; and
  a display for displaying an indication of a result of each analysis.

10 Claims, 7 Drawing Sheets

BODILY FLUID ANALYSIS DEVICE

CROSS REFERENCE TO RELATED APPLICATIONS

The present application is a U.S. National Phase Application pursuant to 35 U.S.C. §371 of International Application No. PCT/EP2012/055256 filed Mar. 22, 2012, which claims priority to European Patent Application No. 11159864.5 filed Mar. 25, 2011. The entire disclosure contents of these applications are herewith incorporated by reference into the present application.

FIELD OF INVENTION

This invention relates to a bodily fluid analysis device.

BACKGROUND

Many people are required to perform regular tests on their blood or other bodily fluid in order to monitor a disease and adjust medication appropriately. For example, diabetes sufferers may be provided with quantities of insulin, for instance by injection, sometimes a number of times daily. The quantity of insulin that is appropriate depends on the person's blood glucose level, so blood glucose level measurement can also occur a number of times daily.

Blood glucose level measurement typically is a multi stage process requiring a number of separate pieces of equipment. A user may be required to carry around a bulky electronic blood glucose meter as well as a supply of test strips and lancet. After lancing the skin to elicit a blood sample, a user must transfer the blood to the test strip, activate the meter and present or insert the test strip into the meter in order to obtain a measurement.

U.S. Pat. No. 7,378,007 B2 discloses a device having a lancet and electrochemical sensor for measuring a blood glucose level. In particular, this document discloses (see column 8) that the sensor and display of the device are disposed on or within a main housing of the device. Separate from the main housing of the device is a sensor disk supporting a plurality of radially arranged sensors. The sensor disk is secured to a spacer ring which is in connection with the main housing via a cam ring. The cam ring may be secured to the main housing by a screw or similar fastening. Thus U.S. Pat. No. 7,378,007 B2 discloses a complex, multi-part device in which various components of the device are supported on separate substrates which are then assembled together.

U.S. Pat. No. 7,641,857 discloses a measuring apparatus having a test element containing an analyte. Adjacent to the test element is a detector for detecting for detecting, optically or electrochemically, a change in the test field and generating an electrical signal. This electrical signal is used to form a measurement result. This document discloses no other detectors or electrical signals.

SUMMARY

A first aspect of the invention provides an apparatus comprising a substrate, the substrate having supported thereon:
plural collectors each for collecting a bodily fluid from the surface of a body part placed adjacent thereto;
at least two pairs of electrodes integral with each of the collectors;
an analyser for analysing each collected bodily fluid, wherein the analyser comprises a controller, wherein each of the at least two pairs of electrodes are connected to the analyser and wherein the analyser is configured to analyse at least one electrical signal received via a first pair of the at least two pairs of electrodes; and
a display for displaying an indication of a result of each analysis, wherein the apparatus is configured to activate the analyser in response to a predetermined electrical signal received via a second pair of the at least two pairs of electrodes.

A bodily fluid collecting end of each of the collectors may be covered by a removable seal. Each removable seal may provide a fluid impermeable barrier around the bodily fluid collecting end of the respective collector.

The apparatus may be configured to activate the display in response to a predetermined electrical signal received via the second pair of electrodes. Alternatively, the apparatus may be configured to activate the display in response to a predetermined electrical signal received via a third pair of the at least one pair of electrodes integral with each collector.

Each second pair of electrodes may be located further from a bodily fluid collecting end of the respective collector than each first pair of electrodes. Each third pair of electrodes may be located closer to a bodily fluid collecting end of each collector than each first pair of electrodes.

The apparatus may further comprise an adjustable calibration resistor. The substrate may be disc shaped and the plural collectors may be arranged generally radially on the substrate. The apparatus may further comprise a cover plate and a glue layer disposed between the substrate and the cover plate, wherein the glue layer is structured so as to define a maximum extent of each of the collectors. The cover plate may have a plurality of notches in an outer edge of the cover plate, each notch being aligned with a respective collector.

A second aspect of the invention provides a method for analysing a bodily fluid sample, comprising:
a bodily fluid analysis device receiving a bodily fluid sample at one of a plurality of bodily fluid collectors formed therewith;
the bodily fluid analysis device detecting a predetermined electrical signal received via a second pair of at least two pairs of electrodes integral with each bodily fluid collector;
in response to detecting the predetermined signal, activating a controller and analysing the collected bodily fluid sample using the controller by analysing at least one electrical signal received via a first pair of the at least two pairs of electrodes; and
the bodily fluid analysis device displaying an indication of a result of the analysis.

BRIEF DESCRIPTION OF THE DRAWINGS

Embodiments will now be described, by way of example only, with reference to the accompanying drawings, in which.

DETAILED DESCRIPTION

Figure 1:
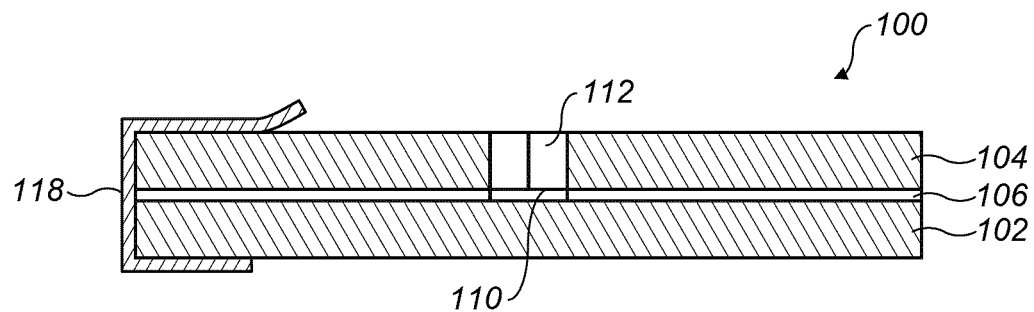
FIG. 1 is a side-on view of a first embodiment of a bodily fluid analysis device according to the invention.
Figure 2:
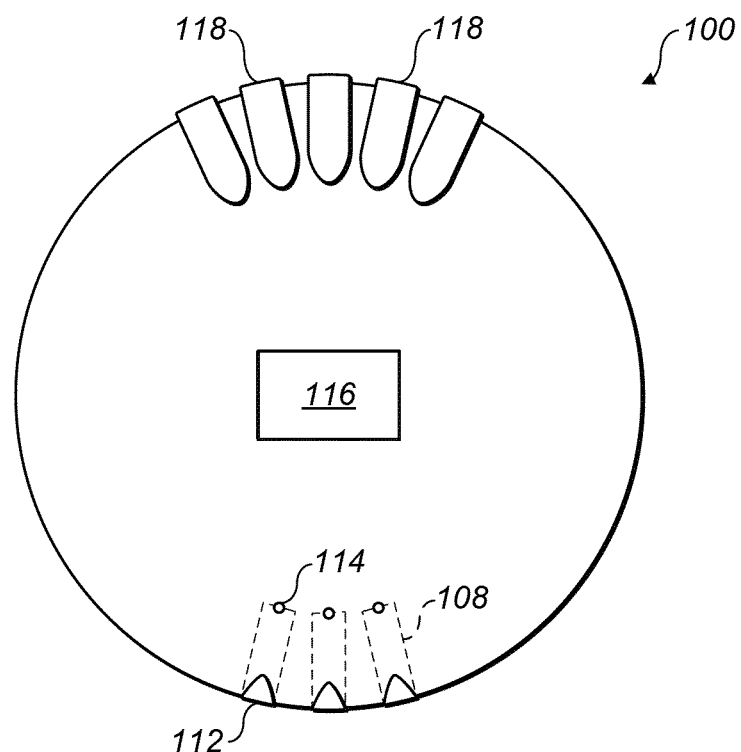
FIG. 2 is a plan view of the bodily fluid analysis device of FIG. 1.

Referring firstly to FIGS. 1 and 2, a side-on view and a plan view respectively of a bodily fluid analysis device 100 are shown. The analysis device 100 has a layered structure. The bottom layer comprises a substrate 102 in the form of a generally circular or disc-shaped sheet material. Formed on top of the substrate 102 are a number of electronic components that are described in detail below with reference to FIG. 3. The top layer of the device 100 comprises at least one cover plate 104 which covers and protects the components formed on top of the substrate 102. Between the substrate 102 and the cover plate 104 is a glue layer 106.

Disposed around the outer edge of the bodily fluid analysis device 100 and on top of the substrate 102 are a number of bodily fluid collection and testing segments 108. Each collection and testing segment 108 has a region of absorbent material 110 extending inwardly from the edge of the bodily fluid analysis device 100. The regions of absorbent material 110 are substantially rectangular in shape, although other shapes are possible. Each region of absorbent material 110 is formed directly onto the substrate 102. The extent of the absorbent material 110 is illustrated by the dashed lines in FIG. 2. Each segment 108 also has at least one pair of electrodes, as described in greater detail below with reference to FIG. 3.

Notches 112 in the form of V-shaped indentations are provided in the outer edge of cover plate 104 at the position of each segment 108. Vent holes 114 are provided in the cover plate 104 at positions coincident with an innermost extent of each region of absorbent material 110. The substrate 102 also supports a display 116. The display 116 is located at or near the centre of the bodily fluid analysis device 100. The bodily fluid analysis device 100 also has removable seals 118 covering each notch 112 and the exposed ends of the regions of absorbent material 110. The removable seals 118 are attached to the underside of the substrate 102, to the upper face of cover plate 104 and to the outer edge of the bodily fluid analysis device 100.

In the view of FIG. 1, only a single exposed collection and testing segment 108 is shown for clarity. The notch 112 and edge of the region of absorbent material 110 of this segment 108 can be seen. However, in reality several segments 108 are visible when the device 100 is viewed edge on. If these segments 108 have had their removable seals 118 removed then the notches 112 and edge of absorbent material 110 is visible. If the removable seal 118 has not been removed, then only the removable seal is visible.

The substrate 102 is formed of a non absorbent material. For example, the substrate 102 may be a plastic material or any other suitable material such as silicon. The substrate is preferably rigid. The cover plate 104 may be formed of any suitable material, for example a rigid or flexible plastic material.

Each of the segments 108 is arranged radially on the bodily fluid analysis device 100. The entire outer edge/circumference of the bodily fluid analysis device 100 may support collection and testing segments 108. Alternatively, the segments 108 may be arranged into two or more groups supported on different parts of the outer edge/circumference of the bodily fluid analysis device 100. The bodily fluid analysis device 100 may support between 15 and 50, preferably between 25 and 35 collection and testing segments 108. Each of the segments 108 contains a region of absorbent material 110 which is also arranged radially on the bodily fluid analysis device 100 such that a first end of the absorbent material 110 is coincident with an outer edge or circumference of the bodily fluid analysis device 100. This first end of the absorbent material 110 is the bodily fluid collecting end and is exposed at the circumference of the bodily fluid analysis device 100 as shown in FIG. 1. The absorbent material 110 may be formed directly onto the substrate 102 or may be glued or otherwise secured to the substrate 102. The absorbent material 110 may be disposed within the glue layer 106, such that it is abutted on either side by the glue layer 106. The notches 112 are formed in the cover plate 104 directly above the location where each region of absorbent material 110 meets the outer edge or circumference of the bodily fluid analysis device 100. The notches 112 extend through the whole thickness of the cover plate 104 such that a portion of the top surface of the absorbent material 110 is exposed.

The absorbent material 110 may be a wicking material having a capillary structure. The absorbent material 110 may be a sheet material. Fluid applied to the exposed part of the absorbent material 110 is drawn into the body of the absorbent material 110 by capillary action. The vent holes 114 extend through the whole thickness of the cover plate 104 such that they contact each region of absorbent material 110 at an end of the absorbent material 110 opposed to the outer, exposed edge. The vent holes 114 facilitate the capillary action by allowing air within the absorbent material 110 to be displaced by fluid.

The absorbent material 110 may contain a chemical substance such as an enzyme. The absorbent material 110 may be doped with the chemical substance during manufacture. When bodily fluid is absorbed into the material 110, it reacts with the chemical substance to create an electrical signal. The chemical substance present in the absorbent material 110 may be selected to react with specific target substance in the bodily fluid or to catalyze a reaction involving a target substance in the bodily fluid. For example, the bodily fluid may be blood and the target substance may be blood glucose. The blood glucose may react with a mediator in the absorbent material 110. For example, the mediator may oxidize the glucose and may subsequently be reoxidised at the anode to produce electrical charge, and—with a corresponding redox-reaction at the cathode—a current. The mediator may be any suitable substance, for example Ferricyanide/Ferrocyanide. An enzyme, for example glucose oxidase, may be involved in the oxidation and reduction of the glucose. The target substance may be another component of blood, for example glycated haemoglobin (HbA1c) or a ketone.

The chemical substance may be present throughout the absorbent material 110 or it may only be present in a portion of the absorbent material 110. In some embodiments, the absorbent material 110 is configured to absorb a predetermined amount of fluid. Depending on the bodily fluid which is being absorbed, the property of the fluid which is to be measured and the method by which the measurement is to be taken, the volume of fluid present in the absorbent material 110 may affect the measurement. Configuration of the absorbent material 110 to absorb a predetermined amount of fluid helps to improve measurement accuracy.

The display 116 may be a Liquid Crystal Display (LCD), comprising an LCD fill (not shown) and a LCD cover plate (not shown). The display 116 may alternatively be another type of suitable electronic display. The display 116 is configured to display a result of a measurement of a target substance in the bodily fluid.

The removable seals 118 may be made of a metal foil and may be impermeable to gas and/or liquid. A removable seal may be secured to the bodily fluid analysis device 100 so as to cover the notch 112, exposed parts of the region of absorbent material 110 and the vent hole 114 such that no fluid is able to enter or leave the absorbent material 110 before the seal 118 is removed. Thus, the humidity (or absence of humidity) within the absorbent material 110 at manufacture is maintained until the time of use of the respective collection and testing segment 108. The removable seals 118 may be secured to the surface of the bodily fluid analysis device 100 by an adhesive. The removable seals 118 may each have an unsecured portion or lip which can be grasped by a user of the bodily fluid analysis device 100 and pulled in order to remove the seal 118. Each collection and testing segment 108 has its own removable seal 118 such that the removal of one seal 118 does not cause any exposure of the absorbent material 110 of another segment 108.

Figure 3:
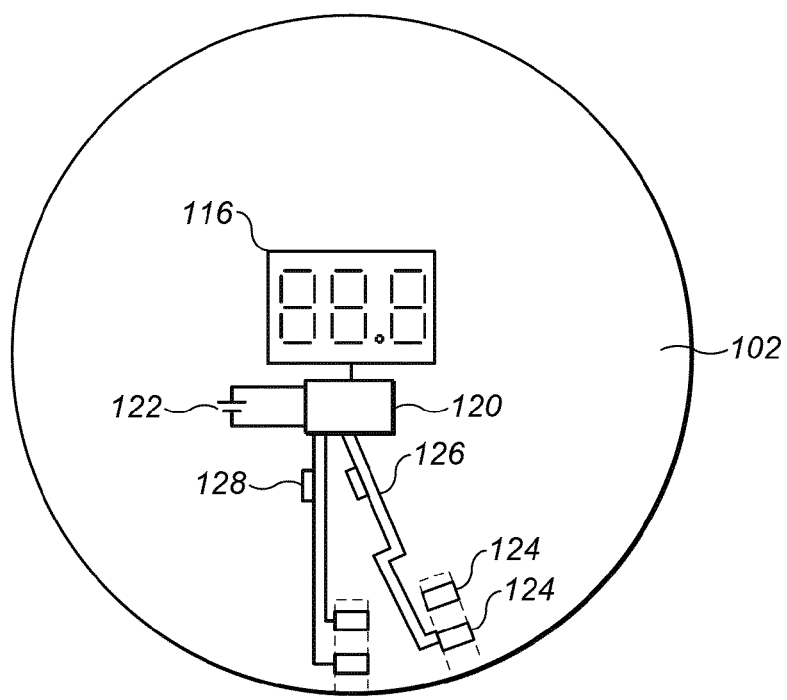
FIG. 3 is a schematic illustration of some of the components of the bodily fluid analysis device of FIGS. 1 and 2.

Referring now to FIG. 3, a schematic view is shown in which electronic components supported on the substrate 102 are illustrated. In FIG. 3, the upper surface of the substrate 102 is shown. The substrate supports a controller 120, display electronics 116 and batteries 122. Each collection and testing segment 108 has a pair of measurement electrodes 124. The controller 108 is connected to each pair of measurement electrodes 124 via conductive paths 126. Each pair of measurement electrodes 124 overlaps with a respective region of absorbent material 110, the extent of which is illustrated by the dashed line. The display 116, controller 120 and batteries 122 are all located at or near the centre of the bodily fluid analysis device 100. A calibration resistor 128 is disposed on a conductive path linking the controller 120 to one of the measurement electrodes 124. The controller 120 is also connected to the display 116 via one or more conductive paths. The batteries 122 are disposed on a conductive path which begins and ends at the controller 120.

The controller 120 is configured to receive electrical signals from the measurement electrodes 124 and to send control signals to the display 116. The measurement electrodes 124 may be made of any conductive material, for example carbon or a metal.

The controller 120 may be a microcontroller or integrated circuit of any suitable type. The controller 120 may store software or algorithms in flash memory (not shown) and may have volatile memory such as RAM (not shown) for executing the software. The controller 120 is connected to each pair of measurement electrodes 124 in order to measure a property of the bodily fluid sample absorbed in the respective region of absorbent material 110.

The batteries 122 are configured to provide power to the controller 120 and the display 116. In some embodiments, the batteries 122 have an energy storage capacity which is sufficient only to power the controller 120 and to power the display 116 for a reasonable time, e.g. up to one hour. As the device 100 requires only a small amount of power, the batteries 122 may be replaced with another source of power such as a capacitor able to collect energy from radio frequency signals emitted by a mobile transmitting device such as a mobile phone. Thus a user of the device 100 may be able to power or charge the device 100 using an application on their mobile phone or the device 100 may charge by being in close proximity to the user's mobile phone for a short time. The device 100 may also be able to collect energy from ambient electromagnetic radiation. In some embodiments, the batteries 122 are replaced with means for collecting energy from a user of the device 100. For example the device 100 may have an area which the user compresses between their fingers to impart energy to the device 100. Alternatively the device 100 may contain both batteries 122 and other means for collecting energy.

The measurement electrodes 124 are disposed directly onto the substrate 102 and overlap with at least a portion of the absorbent material 110. The absorbent material 110 may be applied to the substrate 102 after the measurement electrodes 124. The measurement electrodes 124 may comprise a pair of electrodes spaced apart. The space between the electrodes 124 is at least partially occupied by absorbent material 110. The measurement electrodes 124 are configured to transmit electrical signals generated by the reaction of bodily fluid with a chemical substance present in the absorbent material 110 to the controller 120 so that a property of the bodily fluid can be measured. This property may be a concentration of a specific substance present in the bodily fluid.

Each resistor 128 is disposed on a conductive path linking the controller 120 to one of the measurement electrodes 124. This allows the electrical resistance of the circuit path formed by the controller 120, measurement electrodes 124 and absorbent material 110 to be predetermined. The controller 120 may rely on having an accurate value for the resistance of this circuit path in order to produce an accurate measurement. The resistors 128 may be printed circuit resistors and may be printed on the substrate 102 with a carbon containing ink, for example.

The resistors 128 may be used for calibration, for example to adjust a lot to lot manufacturing accuracy of the device 100. For example, after determining a calibration value of a lot of bodily fluid analysis devices 100 during production, the resistance of the resistor 128 may be adjusted by laser cutting or by modifying the printing process of resistor 128. The resistance of resistor 128 may be used during use of device 100 as a calibration value to adjust a measurement result.

In alternative embodiments, a single resistor 128 is disposed on a conductive path that begins and ends at the controller 120 and does not incorporate any of the pairs of measurement electrodes 124.

As previously mentioned, the volume of bodily fluid absorbed by the absorbent material 110 may, in some measurement techniques and for some target substances, affect the measurement of that target substance. The absorbent material 110 may therefore be manufactured to absorb a predetermined amount of fluid. This amount may depend on the structure and number of capillaries which form the absorbent material 110. The concentration of chemical substance embedded in the absorbent material 110 and which reacts with the target substance in the bodily fluid may also affect the measurement of the target substance. Although efforts may be made to ensure that each device 100 is identical and each piece of absorbent material 110 used in these devices 100 is identical, there may be some batch variation in the absorptive capacity and chemical substance concentration within the absorbent material 110, particularly when the devices are mass produced. Further, variation in the geometry due to manufacturing tolerances may effect the measurement.

During manufacture, one device 100 of each batch may be tested after it has been manufactured in order to determine a calibration value for the devices produced in that batch. In order for the device 100 to be able to produce an accurate measurement of a property of absorbed bodily fluid, the electrical resistance of the measurement circuit path may need to be accurate within a small tolerance. This may be achieved by measuring a control solution with an accurate concentration of analyte, such as glucose. In some embodiments, if an adjustment of the electrical resistance of the measurement circuit path is required, the resistors 128 can be trimmed with a laser such that their resistance is decreased. After the laser trimming a detached part of the resistor 128 no longer forms a part of the measurement circuit path. In this manner, batch variation in the properties of the absorbent material 110 can be corrected.

In alternative embodiments, a capacitor is used for storing a calibration value on the device 100 instead of a resistor 128. Modifying the capacitor may be done by laser cutting or the printing process during production.

In alternative embodiments, a calibration value may be stored in a non-volatile memory of the device during production, for example in the flash memory. Thus, no dedicated resistor 128 or capacitor may be needed for calibration.

The display 116 may be a numerical display configured to display three digits. In some other embodiments the display 116 may be configured to display more than three digits. The best choice of display depends on the range and accuracy of the measured property required. In some embodiments, the display 116 may be configured to display a decimal point before or after the first or second digit. Alternatively the decimal point may be in a fixed location, for example after the second digit. Each digit of the display 116 may comprise a seven-segment display capable of displaying the numbers 0 to 9. Only a single connection between the controller 120 and the display 116 is shown, however there may be several individual connections. There may be a connection between the controller 120 and the display 116 for each digit, or for each segment of each digit, or there may be a multiplexed connection.

The device 100 is preferably relatively small in size, for example about 80-120 mm in diameter and less than 15 mm thick. This makes the device 100 easily portable for a user such that it may be easily carried around by the user. Because the functions of a test strip and analysis device are combined in a single device of small size, a user does not need to carry a separate meter, which may be a relatively bulky item.

Figure 4:
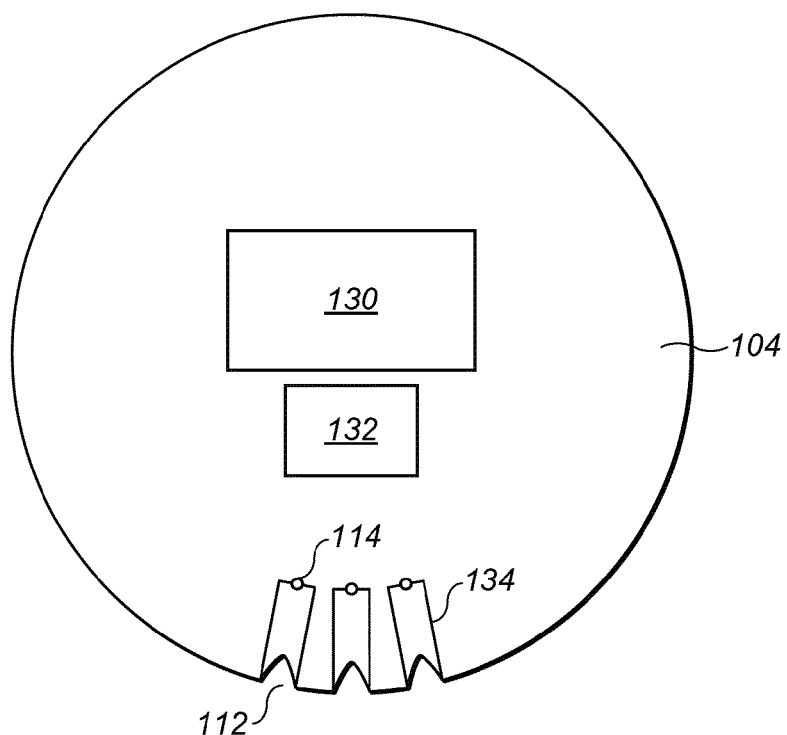
FIG. 4 shows a view of the underside of a cover plate forming part of the bodily fluid analysis device of FIGS. 1, 2 and 3.

Referring now to FIG. 4, a view of the underside of cover plate 104 is shown. Cover plate 104 has a display window 130, a controller and battery cavity 132 and absorbent material cavities 134. Notches 112 are provided in the outer edge of the cover plate 104 and are aligned with each absorbent material cavity 134. The vent holes 114 are provided in the cover plate 104 at the innermost end of each absorbent material cavity 134.

The display window 130, notches 112 and vent holes 114 are cut out portions which are also visible from the upper side of the cover plate 104. The controller and battery cavity 132 and absorbent material cavities 134 are recesses in the underside of the cover plate 104 which do not extend through the whole thickness of the cover plate 104 and are not visible from the upper side. The controller and battery cavity 132 provides a space for the controller 120, batteries 122 and any other electronic components, such as resistors and capacitors, which may form a part of the power and control circuitry. The absorbent material cavities 134 provide a space for the region of absorbent material 110. The absorbent material cavities 134 may be large enough to allow the region of absorbent material 110 to expand when saturated with fluid.

The display window 130 may have a transparent cover, such as a transparent piece of film, in order to protect the display 116 underneath from damage. Alternatively the display 116 may comprise a transparent cover plate (not shown), which may be made of a glass material.

Figure 5:
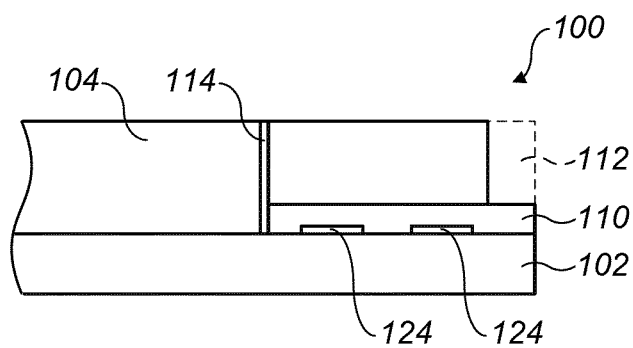
FIG. 5 shows detail of a cross-section of a portion of the bodily fluid analysis device of FIGS. 1 to 3.
Figure 6:
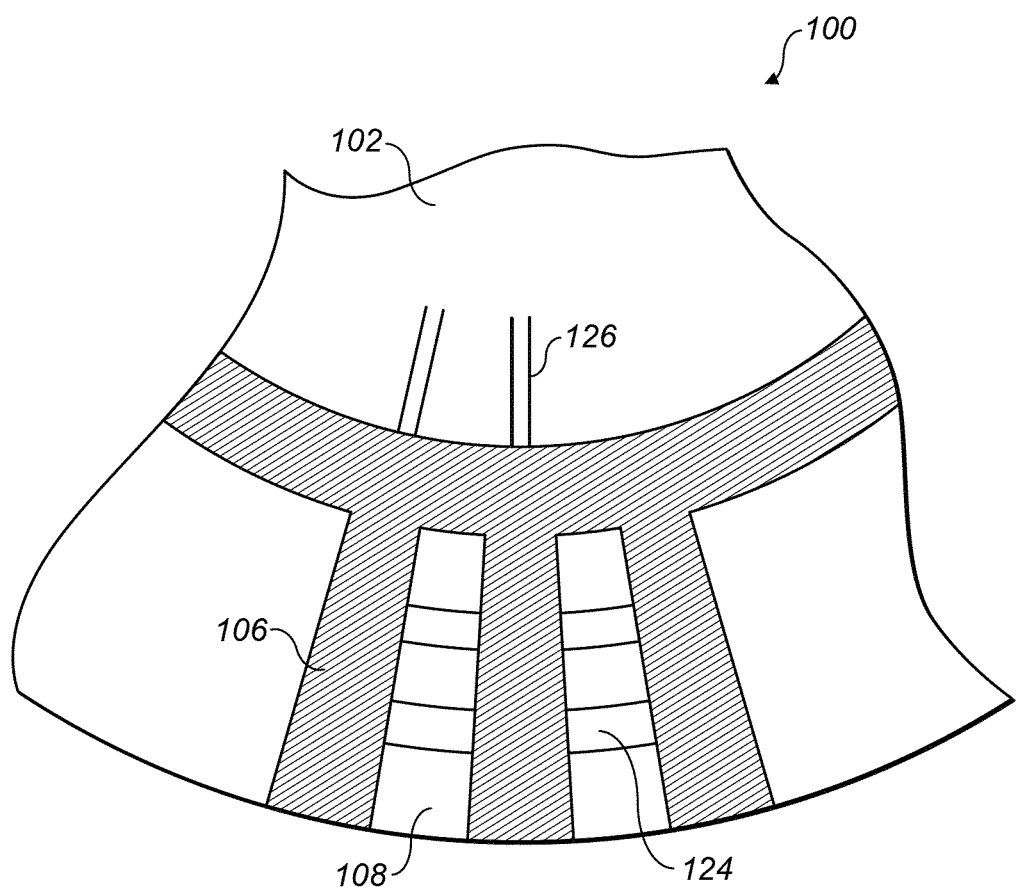
FIG. 6 is a view of the upper side of a substrate forming part of the bodily fluid analysis device of FIGS. 1 to 3 and shows detail of some of the components formed thereon.

Referring now to FIGS. 5 and 6, FIG. 5 shows a detailed cross-sectional view of the bodily fluid analysis device 100 at a position of one of the collection and testing segments 108. The notch 112 in the cover plate 104 exposes some of a top surface of the absorbent material 110. This makes the process of absorption of bodily fluid by the absorbent material 110 more efficient. Measurement electrodes 124 are formed directly onto the substrate 102. The absorbent material 110 may also be formed directly onto the substrate 102 and may overlie the measurement electrodes 124 as shown in FIG. 5. FIG. 6 shows a detailed view of the top surface of the substrate 102 and some of the components supported by the substrate 102. The glue layer 106 is omitted from FIG. 5 for reasons of clarity but is shown in FIG. 6. Exemplary positioning of the measurements electrodes 124 is shown in both FIGS. 5 and 6, however other electrode arrangements are possible as discussed in greater detail below. The glue layer 106 fills the area on the substrate between each collection and testing segment 108. The glue layer covers the conductive paths located between each segment 108. The glue layer 106 secures the cover plate 104 to the substrate 102, but also separates the segments 108 from one another. This ensures that there are no environmental impacts e.g. increased humidity, on a segment 108 when an adjacent segment is exposed and also helps to ensure that no fluid absorbed in one segment 108 can leak into another.

In some embodiments the region of absorbent material 110 may be omitted. The absorbent material 100 may be replaced by a cavity with appropriate dimensions that acts as a capillary. In these embodiments, the glue layer 106 may also perform the function of a spacing layer to ensure that the capillary cavity is of a suitable width.

Figure 7A:
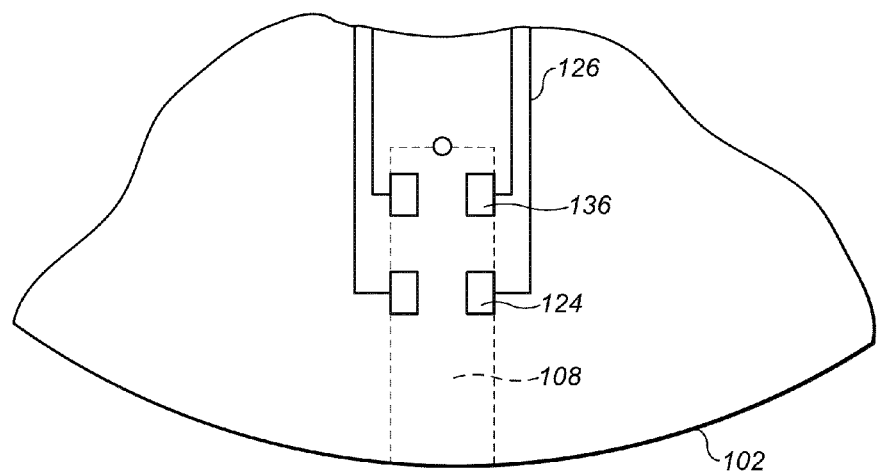
FIGS. 7A and 7B show schematic illustrations of embodiments of the invention containing activation electrodes.
Figure 7B:
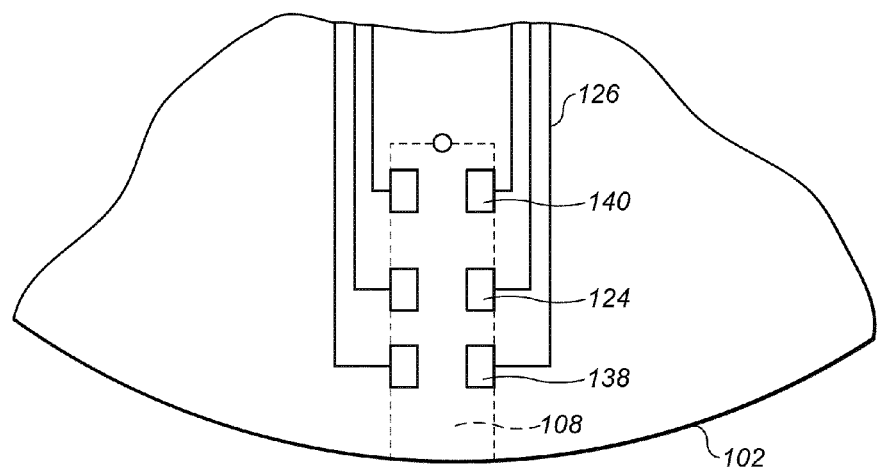

Although only a single pair of electrodes for each collection and testing segment 108 are illustrated in FIGS. 3, 5 and 6, the device 100 may comprise several pairs of electrodes for each segment 108. FIGS. 7A and 7B show schematic illustrations of embodiments of the invention containing activation electrodes.

In FIG. 7A a single collection and testing segment 108 is shown on the substrate 102 for clarity. In this embodiment, the device 100 has a pair of measurement electrodes 124 and a pair of activation electrodes 136. Both the measurement electrodes 124 and the activation electrodes 136 are connected to the controller 120 via conductive paths 126 and overlap the absorbent material 110. In some embodiments the electrodes may only overlap partially with the absorbent material 110. The activation electrodes 136 are configured to pass electrical signals generated in the absorbent material 110 to the controller 120. These signals are used as a trigger for activation of the controller 120 and the display 116. For example, the controller 120 may be configured to detect only signals above a certain threshold which are received from the activation electrodes 136. When a signal above the threshold is detected, the controller 120 and display 116 are activated. The measurement electrodes 124 are located closer to the outer edge of the collection and testing segment 108 than the activation electrodes 136. Therefore, as fluid is absorbed into the absorbent material 110, the region between the measurement electrodes 124 is first saturated and then, provided enough fluid is available, the region between the activation electrodes 136 is saturated. This arrangement ensures that there is a sufficient quantity of bodily fluid in the region between the measurement electrodes 124 when the controller 120 and display 116 are activated.

FIG. 7B shows another embodiment in which there are two pairs of activation electrodes and one pair of measurement electrodes 124. In FIG. 7B a single collection and testing segment 108 is shown on the substrate 102 for clarity. The two pairs of activation electrodes are controller activation electrodes 138 and display activation electrodes 140. The controller activation electrodes 138 are located closest to the outer edge of the collection and testing segment 108. The measurement electrodes 124 are located behind the controller activation electrodes 138; further from the outer edge of the segment 108. The display activation electrodes 140 are located behind the measurement electrodes 124; furthest from the outer edge of the segment 108. In this embodiment, the controller 120 is configured to detect only signals above a certain threshold which are received from the controller activation electrodes 138 and display activation electrodes 140. When a signal above a threshold value is detected via the controller activation electrodes 138, the controller 120 is activated. The controller 120 may then begin recording signals received via the measurement electrodes 124. When a signal above a threshold value is detected via the display activation electrodes 140, the display 116 is activated. The display 116 may be activated in a standby mode. Since the display activation electrodes 140 are located further from the outer edge of the segment 108 than the controller activation electrodes 138, the controller 120 is activated before the display 116. This results in the display 116 being activated for the shortest possible time before a reading is displayed. This reduces the total amount of power required to make a measurement of a property of a bodily fluid and to display the result of the measurement to a user of the device 100 for a given period of time.

The signals from display activation electrodes 140 may also be used in the measurement of an analyte in the bodily fluid. For example, by measuring the time when the bodily fluid reaches the display activation electrodes 140, a measurement of the viscosity or the amount of bodily fluid can be made.

In these embodiments containing activation electrodes, each of the pairs of electrodes are connected to the controller 108 via separate conductive paths 126 formed on the substrate 102. The display 116, batteries 122 and resistor 128 of the device 100 may be substantially the same as when only the measurement electrodes 124 are present. The controller 120 and display 116 only draw power from the batteries 122 when active. When inactive, the current discharge from the batteries 122 is zero or close to zero such that the shelf life of the device 100 is not affected.

Regarding the positioning of the pairs of electrodes within each collection and testing segment 108, in some embodiments, each of the pairs of measurement electrodes 124 and activation electrodes (136, 138, 140) are arranged in parallel with a radial line connecting the segment 108 with a centre point of the device 100, as shown in FIGS. 3, 5 and 6. In some other embodiments, each pair of electrodes is arranged perpendicularly to this radial line. This second arrangement is shown in FIGS. 7A and 7B. The electrodes may be contained completely within the region of absorbent material 110. Alternatively, the electrodes may overlap partially with the absorbent material 110.

In some embodiments, the bodily fluid which is collected by the device 100 is blood and the property of the blood which is measured is the blood glucose level. The process of making a blood glucose level measurement with the device 100 will now be described with reference to FIGS. 8A-D and the flow chart of FIG. 9.

Figure 8A:
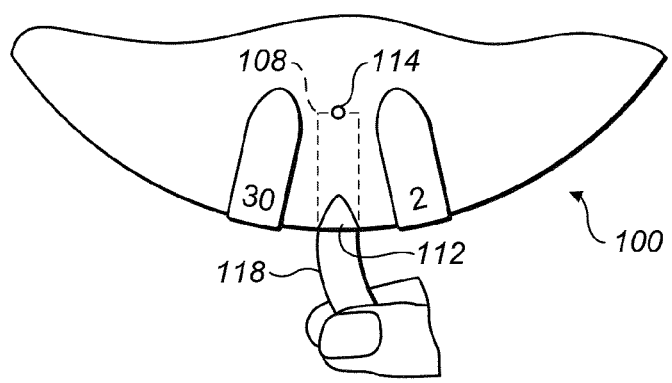
FIGS. 8A-D show the bodily fluid analysis device of FIGS. 1 to 3 in an exemplary operation.

In operation, a user of the device 100 first removes one of the removable seals 118 from its respective collection and testing segment 108, as shown in FIG. 8A. To achieve this, a user grasps and pulls an end of the removable seal 118 which is not secured to the device 100. Removal of the removable seal 118 exposes a notch 112, a portion of the absorbent material 110 and a vent hole 114. The removable seals 118 may be printed with numbers to allow the user to more easily monitor their usage of the device 100. In FIG. 8A the user is removing the first of 30 removable seals 118.

Figure 8B:
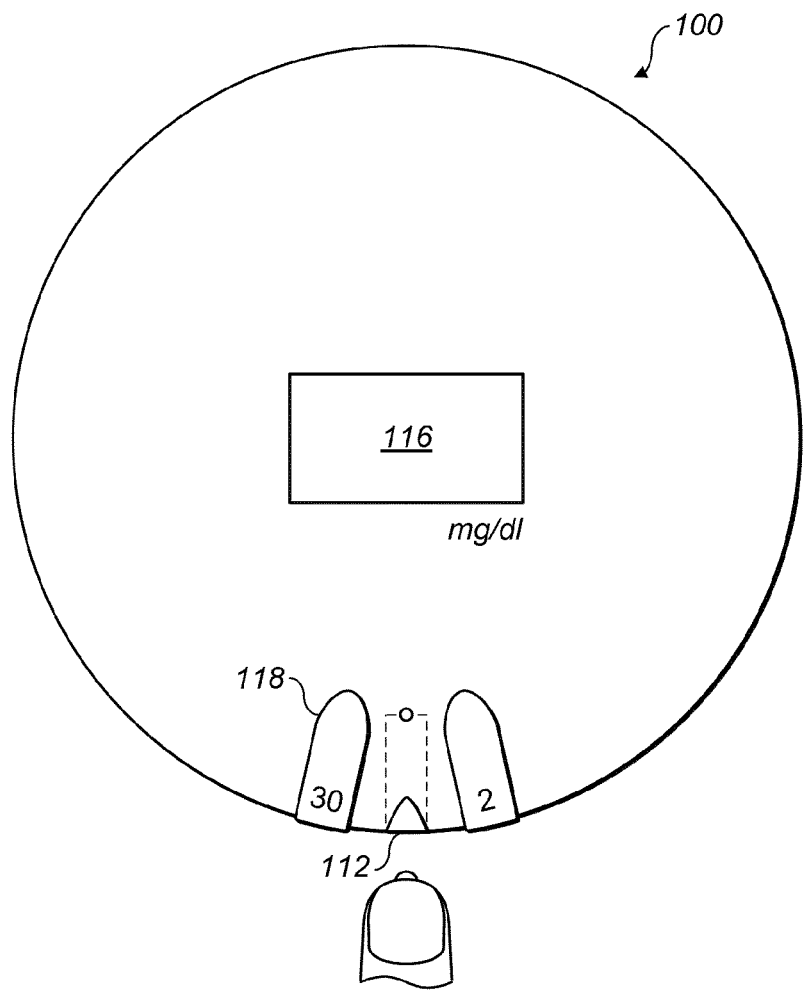

After removing the removable seal 118, the user obtains a blood sample. This can be achieved by the user in any known way, for example by using a lancet or similar to elicit blood from their finger. In FIG. 8B, the user has elicited a blood sample and is about to present the blood to the exposed end of the region of absorbent material 110. Printed on the upper surface of the cover plate 104 is a unit in which the subsequent measurement is expressed. This may for example be mg/dl, mmol/l or mol/l. In some other embodiments this unit may instead be printed on a cover plate (not shown) of the display 116 itself. In some other embodiments, the unit of the measurement may be displayed by the display 116 and may only appear when the result of the measurement is shown.

Figure 8C:
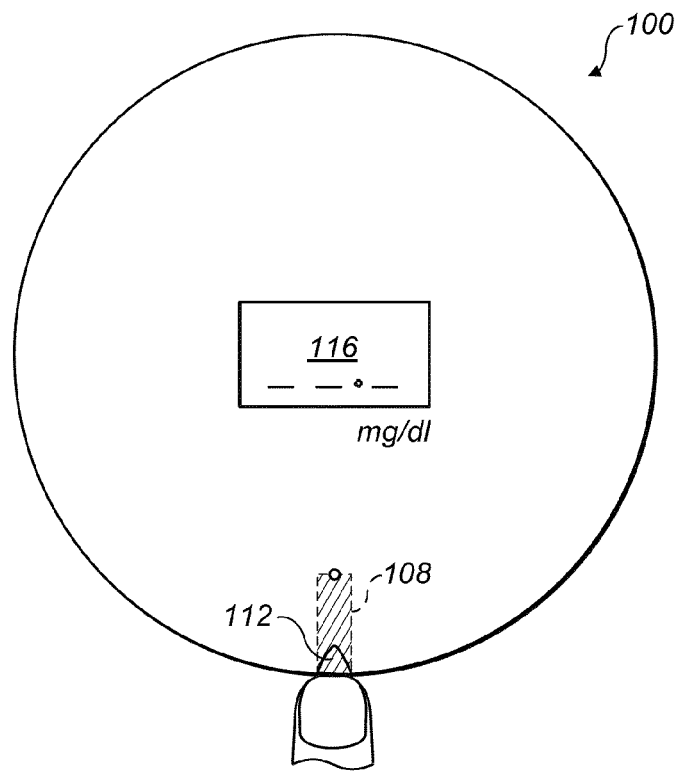

In FIG. 8C, the user has presented the blood to the absorbent material 110 by pressing their finger against the edge of the device 100 at the location of the corresponding notch 112. The alignment of the notch 112 with the absorbent material makes it easier for the user to ensure that they are providing their blood sample onto the absorbent material 110. The notch 112 may also be sized and shaped such that it exerts a pressure on a user's finger at positions either side of the lancing location. This arrangement may aid in expelling blood from the user's finger. The blood is absorbed into the absorbent material 110 by capillary action. The absorbent material 110 becomes saturated with the blood as indicated by the cross hatching. The blood reacts with an enzyme present in the absorbent material 110 or undergoes a reaction which is catalyzed by an enzyme present in the absorbent material 110. This reaction produces an electrical charge which may pass as a current through the measurement electrodes 124 and via the conductive paths 126 to the controller 120. The amount of analyte contained in the bodily fluid determines the magnitude of the electrical signal that reaches the controller 120.

If activation electrodes (136, 138, 140) are present, then when an electrical current above a threshold level passes through the respective activation electrodes (136, 138, 140), the display 116 and controller 120 and are activated. The controller 120 begins measuring signals received from the measurement electrodes 124. To achieve this, the controller 120 executes software and/or algorithms with which it has been programmed. The controller 120 is programmed to interpret signals received via the measurement electrodes 124 so as to make a measurement of a property of the bodily fluid. The controller 120 may produce a measurement based on a single signal sample received via the measurement electrodes 124. Alternatively the controller 120 may record a series of signals received via the measurement electrodes 124. The controller 120 may compute a measurement based on an analysis of the series of received signals. The property of the electrical signal measured at the controller 120 may be a current and/or voltage of the signal and may involve a time element, for instance by integrating an electrical parameter over time.

If the display 116 has been activated, but the measurement is not yet complete, then the display 116 may show a standby state, for example by illuminating the bottom segment of each digit of the display 116, as shown in FIG. 8C.

Figure 8D:
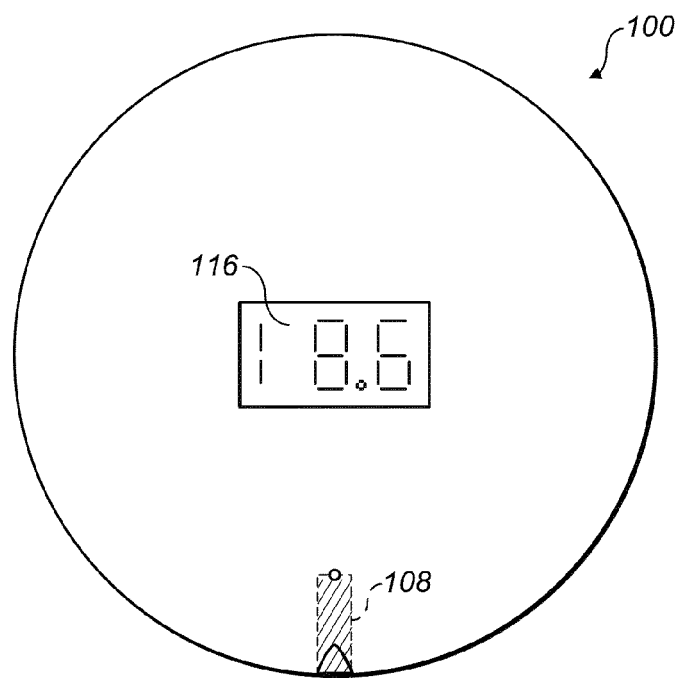

In FIG. 8D, the controller 120 has finished making its measurement of the blood glucose level of the absorbed blood sample. The controller 120 controls the display 116 to display the result of the measurement to the user. The display 116 continues to display the result of the measurement for a predetermined amount of time, for example 60 seconds.

Figure 9:
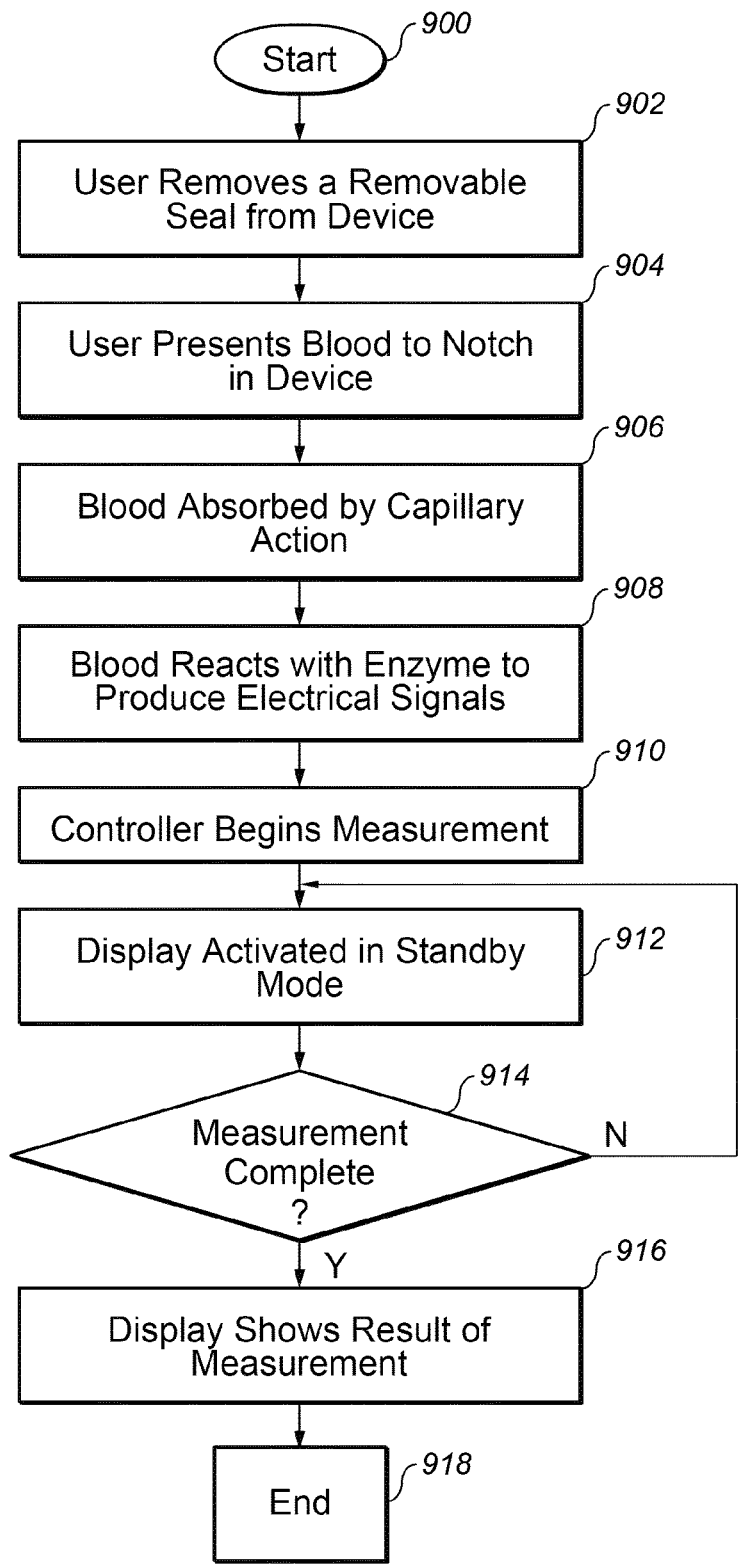
FIG. 9 is a flow chart illustrating an exemplary operation of the bodily fluid analysis device of FIGS. 1 to 3.

FIG. 9 is a flow chart illustrating the process of measuring a blood glucose level using the device 100. The process begins at step 900. At step 902 the user removes a removable seal 118 from the device 100. This step of the process is shown in FIG. 8A. At step 904 the user presents blood to the device 100 by pressing their finger against the notch 112. This step of the process is shown in FIG. 8C.

At step 906 the blood is absorbed into the device 100 by capillary action. The capillary action causes the blood to fill all of the absorbent material 110 such that it becomes saturated. At step 908 the blood reacts with a chemical substance embedded in the absorbent material 110. Specifically, the glucose in the blood reacts with an enzyme, for example glucose oxidase or glucose dehydrogenase. The reaction produces electrical charge which flows as a current through the saturated absorbent material 110 to the measurement electrodes 126.

At step 910, the controller 120 begins measuring the blood glucose level in the absorbed blood sample. The controller 120 is configured to receive electrical signals produced by the reaction of the blood glucose with the enzyme in the absorbent material 110 via the measurement electrodes 124. The controller 120 may receive multiple signals in order to make the measurement. The signals may for example be multiple consecutive values of a voltage or a current separated over time. The measurement may involve a time element, for instance integrating the values over time.

At step 912 the display 116 is activated. When initially activated the display 116 may be in a standby mode. This standby mode may consist of illuminating at least some of the pixels of the display. This has the added advantage of signalling to a user of the device 100 that the blood sample they have provided is of a sufficient volume and quality and that a measurement is underway. This step of the process is shown in FIG. 8C. Steps 910 and 912 may occur substantially simultaneously.

If the device 100 includes activation electrodes (136, 138, 140), then steps 910 and 912 may only begin once it is determined that an electrical signal received at the controller 120 via the activation electrodes is above a threshold level. This determination may be performed in hardware at the controller 120 such that the controller 120 may remain inactive during the determination. The device 100 may be configured such that when the absorbent material 110 is saturated with a blood sample of a sufficient quality, the threshold signal value is exceeded. If, after a time, no measurement result is displayed or the display 116 remains in a standby mode, this may indicate to a user that not enough blood has been absorbed or that the reaction rate is too low.

If both controller activation electrodes 138 and display activation electrodes 140 are present then each of steps 910 and 912 may be preceded by separate signal threshold determination steps.

At step 914 it is determined if the measurement of the blood glucose level is complete. In some embodiments, the controller 120 may perform the measurement relatively quickly based on a single or a few signals from the measurement electrodes 124. In some other embodiments the controller 120 may record signals over a short period of time in order to produce a more accurate measurement of the blood glucose level. If the measurement is not complete, the display continues to operate in standby mode at step 912. Once it is determined that the measurement is complete the process continues at step 916.

At step 916 the display 116 is caused by the controller 120 to display a result of the measurement. The display 116 may continue to display the result of the measurement for a predetermined period of time before deactivating the display 116. This step of the process is shown in FIG. 8D. The process ends at step 918. After the user has used all of the collection and testing segments 108 on the device 100, the device 100 may be discarded.

It will be appreciated that the above described embodiments are purely illustrative and are not limiting on the scope of the invention. Other variations and modifications will be apparent to persons skilled in the art upon reading the present application. For example, although the invention has been described with respect to a blood glucose meter, the teachings herein are applicable to the measurement of parameters of other bodily fluids, such as plasma, tears or saliva. Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. An apparatus comprising a substrate, the substrate having supported thereon:
   plural collectors each for collecting a bodily fluid from the surface of a body part placed adjacent thereto;
   at least two pairs of electrodes integral with each of the collectors;
   an analyzer for analyzing each collected bodily fluid, wherein the analyzer comprises a controller, wherein each of the at least two pairs of electrodes are connected to the analyzer and wherein the analyzer is configured to analyze at least one electrical signal received via a first pair of the at least two pairs of electrodes; and
   a display for displaying an indication of a result of each analysis, wherein the apparatus is configured to activate the analyzer in response to a predetermined electrical signal received via a second pair of the at least two pairs of electrodes, and
   wherein the controller comprises memory having stored thereon software instructions that, if executed by the controller,
   cause the controller to activate the display in response to a predetermined electrical signal received via a third pair of the at least two pairs of electrodes integral with each collector.

2. An apparatus according to claim 1, wherein a bodily fluid collecting end of each of the collectors is covered by a removable seal.

3. An apparatus according to claim 2, wherein each removable seal provides a fluid impermeable barrier around the bodily fluid collecting end of the respective collector.

4. An apparatus according to claim 1, wherein each second pair of electrodes is located closer to a bodily fluid collecting end of the respective collector than each first pair of electrodes.

5. An apparatus according to claim 1, wherein each third pair of electrodes is located further from a bodily fluid collecting end of each collector than each first pair of electrodes.

6. An apparatus according to claim 1, wherein the apparatus further comprises an adjustable calibration resistor.

7. An apparatus according to claim 1, wherein the substrate is disc shaped and the plural collectors are arranged generally radially on the substrate.

8. An apparatus according to claim 1, wherein the apparatus comprises a cover plate and a glue layer disposed between the substrate and the cover plate, wherein the glue layer is structured so as to define a maximum extent of each of the collectors.

9. An apparatus according to claim 8, wherein the cover plate has a plurality of notches in an outer edge of the cover plate, each notch being aligned with a respective collector.

10. A method for analysing a bodily fluid sample, comprising:
- a bodily fluid analysis device receiving a bodily fluid sample at one of a plurality of bodily fluid collectors formed therewith;
- the bodily fluid analysis device detecting a predetermined electrical signal received via a second pair of at least two pairs of electrodes integral with each bodily fluid collector;
- in response to detecting the predetermined signal via the second pair of electrodes, activating a controller and analyzing the collected bodily fluid sample using the controller by analysing at least one electrical signal received via a first pair of the at least two pairs of electrodes;
- the bodily fluid analysis device detecting a predetermined electrical signal received via a third pair of at least two pairs of electrodes integral with each bodily fluid collector;
- in response to detecting the predetermined signal via the third pair of electrodes, activating a display of the bodily fluid analysis device; and
- the bodily fluid analysis device displaying an indication of a result of the analysis.

\* \* \* \* \*